US007824697B2

(12) United States Patent
Trissel et al.

(10) Patent No.: US 7,824,697 B2
(45) Date of Patent: Nov. 2, 2010

(54) HIGH CONCENTRATION BACLOFEN PREPARATIONS

(75) Inventors: Lawrence A. Trissel, Sapphire, NC (US); Yanping Zhang, Missouri City, TX (US)

(73) Assignee: Board of Regents, The University of Texas System, Austin, TX (US)

(*) Notice: Subject to any disclaimer, the term of this patent is extended or adjusted under 35 U.S.C. 154(b) by 1260 days.

(21) Appl. No.: 11/156,370

(22) Filed: Jun. 17, 2005

(65) Prior Publication Data

US 2006/0009523 A1 Jan. 12, 2006

Related U.S. Application Data

(60) Provisional application No. 60/587,274, filed on Jul. 12, 2004.

(51) Int. Cl.
*A61K 9/00* (2006.01)
*A01N 37/12* (2006.01)

(52) U.S. Cl. .................................. 424/400; 514/567
(58) Field of Classification Search ............ 424/400; 514/567

See application file for complete search history.

(56) References Cited

U.S. PATENT DOCUMENTS

| 5,149,713 | A | 9/1992 | Bousquet | |
|---|---|---|---|---|
| 2004/0062819 | A1* | 4/2004 | Hildebrand | 424/680 |

OTHER PUBLICATIONS

Physicians' Desk Reference, (Lioresal® Intrathecal, 1995, Medical Economics Data Production Company, 49th edition, 1487-1489.*
Baum, S. and Schuster, F., "Production and Testing of Baclofen Solutions," Pharmazeutische Zeitung, vol. 133, Germany, pp. 28-32 (1988).
Diogenes Record No. 2905396, MDR Report: Neurological Division, Medtronic, Inc. Indura LKK, Model #8731 (2008).
Diogenes Record No. 2779300, MDR Report: Medtronic, Inc. Synchromed B Pump, Intrathecal, Model #8267 (2007).
Diogenes Record No. 2596683, MDR Report: Rice Creek Manufacturing Indura Catheter, Model #8709 (2006).
Ridley, B. and Rawlins, P., "Intrathecal Baclofen Therapy: Ten Steps Toward Best Practice," Journal of Neuroscience Nursing: 38:2, pp. 72-82 (2006).
International Search Report dated Sep. 5, 2005.
Ahuja S., "Baclofen," *Analytical Profiles of Drug Substances*, vol. 14, New York: Academic Press, pp. 527-548, 1985.
Allen L. V., et al., "Stability of Baclofen, Captopril, Diltiazem Hydrochloride, Dipyridamole, and Flecainide Acetate is Extemporaneously Compounded Oral Liquids", *Am J Health-Syst. Pharm.*, 53:2179-2184, 1996.
Cruaud et al., "The Characterization and Release Kinetics Evaluation of Baclofen Microspheres Designed for Intrathecal Injection", *Int. J. Pharmacuetics*, 177, 247-257), 1999.
Gupta V. D., Parasrampuria J., "Quantitation of 4-(4-chlorophenyl)-2-pyrrolidine in baclofen powder and tablets," *Drug Develop. Indust. Pharm.*, 14: 1623-1628, 1998.
Holloway, R. H., "Systemic Pharmacomodulation of Transient Lower Esophageal Sphincter Relations," *Amer. J. Medicine*, 111:8A, 178S-185S, 2001.
Johnson C. E., et al., "Stablility of an extemporaneously compounded baclofen oral liquid", *Am. J. Hosp. Pharm.*, 50:2353-55, 1993.
Lioresal Intrathecal package insert, Medtronic Neurological, Minneapolis, Minnesota, Apr. 1997.
McEvoy G., *AHFS Drug Information 2004*, Bethesda, MD: American Society of Health-System Pharmacists, 2004, pp. 1324-1328 only.
Sitaram B.R., Tsui M., Rawicki H. B., et al., "Stability and compatibility of intrathecal admixtures containing baclofen and high concentrations of morphine", *Int. J. Pharm.*, 153: 13-24, 1997.
United States Pharmacopeia 27$^{th}$ ed., Rockville, MD: United States Pharmacopeial Convention, 2004.
USP Dictionary of USAN and International Drug Names 2003, Rockville, MD: United States Pharmacopeial Convention, 2003.
Cardiff, L and Rieck, A.M., "Concentrating on Baclofen," Australian Journal of Hospital Pharmacy, Feb. 1995, vol. 25, No. 1, pp. 102-103 (abstract).

* cited by examiner

*Primary Examiner*—Frederick Krass
*Assistant Examiner*—Gigi Huang
(74) *Attorney, Agent, or Firm*—Vinson & Elkins LLP

(57) ABSTRACT

Stable aqueous solutions comprising concentrations of baclofen in the range of greater than 2.0 mg/mL up to about 10 mg/mL are disclosed. These solutions can be used as pharmaceuticals for parenteral or oral administration. The invention also provides methods of preparing said stable aqueous baclofen solutions.

4 Claims, No Drawings

HIGH CONCENTRATION BACLOFEN PREPARATIONS

CROSS-REFERENCE TO RELATED APPLICATIONS

This application claims the benefit of U.S. Provisional Application No. 60/587,274, filed Jul. 12, 2004.

BACKGROUND OF THE INVENTION

1. Field of the Invention

The invention relates to aqueous solutions comprising high concentrations of baclofen in the range of greater than 2.0 mg/mL up to about 10 mg/mL. These solutions can be used as pharmaceuticals. The invention also relates to various methods of preparing stable solutions in this concentration range.

2. Background

Baclofen is a skeletal muscle relaxant and antispastic agent. Baclofen is a structural analog of the inhibitory neurotransmitter gamma-aminobutyric acid (GABA), and may exert its effects by stimulation of the $GABA_B$ receptor subtype. Baclofen is the generic (USAN) name (USP Dictionary of USAN and International Drug Names 2003) for 4-amino-3-(p-chlorophenyl) butyric acid, a derivative of γ-aminobutyric acid. Its structural formula is:

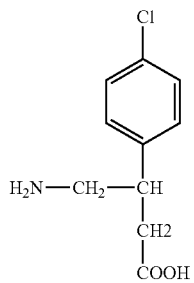

Baclofen is a white to off-white, odorless or practically odorless crystalline powder, with a molecular weight of 213.66. It is slightly soluble in water, very slightly soluble in methanol, and insoluble in chloroform. Its slight solubility in water makes it difficult to obtain stable aqueous solutions of baclofen that have concentrations greater than approximately 2 mg/mL.

Baclofen can be administered orally, but when injected directly into the intrathecal space of a patient effective CSF concentrations are achieved with resultant plasma concentrations 100 times less than those occurring with oral administration. Baclofen injections (Lioresal Intrathecal, Medtronic) are therefore commonly administered intathecally via an implanted pump to manage severe spasticity of spinal cord origin. (McEvoy, 2003) Presently, baclofen is commercially available for injection as a 2 mg/mL solution having a pH of 5 to 7 and the following simple preservative-free formula (Lioresal Intrathecal package insert):

| Baclofen | 2 mg |
|---|---|
| Sodium chloride | 9 mg |
| Water for injection | qs 1 mL |

Unfortunately, the 2 mg/mL concentration has been inadequate to control the pain and symptoms of some patients. An additional difficulty is that mixing a 2 mg/mL baclofen injection with other drugs such as morphine or hydromorphone in "cocktails" to aid in control of pain can dilute the baclofen content to unacceptably low levels. In these and other applications, it can be desirable to administer a more concentrated solution of baclofen in order to reduce the volume of baclofen solution to be administered. But due to baclofen's slight solubility in water, aqueous solutions having a higher concentration of baclofen have not been shown to be commercially viable products. At higher concentrations baclofen may not entirely dissolve in aqueous solution, or it may have an unacceptable tendency to precipitate out of solution during storage.

An upper limit on room temperature aqueous solubility of baclofen has been reported by some sources as 4.3 mg/mL (Ahuja, 1985), however that concentration was achieved by allowing the baclofen to dissolve over a period of weeks or months until it reached an equilibrium state. In an equilibrium solution there is always particulate baclofen present. The solution is at equilibrium because the rate at which the baclofen particulates dissolve is equal to the rate at which the dissolved baclofen precipitates out of solution.

Baclofen has not been shown to be nearly as soluble when less time-consuming methods are used to dissolve it, nor has it been reported that concentrations equaling or even approaching the 4.3 mg/mL concentration can be achieved in solutions that are not at equilibrium, i.e. where no particulate baclofen is present. Commercially and pharmaceutically acceptable baclofen solutions must not contain any significant amount of particulates, and the baclofen must stay in solution without precipitating prior to and during administration to a patient. Only solutions of baclofen having a concentration of 2 mg/mL have previously been demonstrated to have the properties that make them an acceptable commercial pharmaceutical product by remaining stable for extended periods of time without precipitation of significant amounts of baclofen particulates.

Various sources have reported stable suspensions or syrups of baclofen for oral administration that had concentrations even higher than equilibrium concentration of 4.3 mg/mL, (Allen et al., 1996; Johnson and Hart, 1993) but none of these preparations are acceptable for pharmaceutical injection uses. Other sources have reported the production of microspheres containing 12 to 50% baclofen (Cruaud et al., 1999, but such microspheres are not compatible with delivery systems requiring an aqueous solution of baclofen.

It was also known that baclofen can be readily dissolved in very high and very low pH solutions. For example, Ahuja (1985) reported that concentrations of baclofen greater than 20 mg/ml could be obtained by dissolving baclofen in aqueous solutions of 0.1N HCl or aqueous solutions of 0.1N NaOH. Significantly, the $pKa_1$ for baclofen at 20° C. is reported by Ahuja to be 3.87±0.1 and the $pKa_2$ at 20° C. 9.62±0.1. The pH of a 0.1N HCl solution is well below the $pKa_1$ value for baclofen and the pH of a 0.1N NaOH solution is well above the $pKa_2$ value for baclofen. Thus baclofen at these pHs would be expected to have different solubility properties than baclofen dissolved in more neutral pH solutions. Moreover, it would be expected that high concentration solutions of baclofen that were prepared at pHs below $pKa_1$ or above the $pKa_2$ value of baclofen would tend to fall out of solution when the pH of the solution was adjusted to a value between the $pKa_1$ and $pKa_2$ values. Because solutions having a pH of less than 4 or greater than 8.5 would not expected to be acceptable pharmaceutically, the use of very high or very low pH solutions of baclofen does not resolve the need for higher concentration aqueous solutions of baclofen.

Therefore, there appears to be a clinical need for more concentrated aqueous solutions of baclofen having acceptable pharmaceutical properties, and most preferably for concentrated solutions that are also stable in a variety of storage conditions and for extended periods of time.

BRIEF SUMMARY OF THE INVENTION

The present invention provides high-concentration, aqueous solutions of baclofen, including solutions that are stable under a variety of storage conditions and for extended periods of time. The present invention also provides methods for preparing such compositions.

DETAILED DESCRIPTION OF THE INVENTION

Preferred embodiments include stable, high-concentration baclofen solutions suitable for therapeutic use and methods of preparing such solutions. Other preferred embodiments provide methods for enhancing or accelerating the solubilization of baclofen solutions.

Commercially available lower-concentration baclofen solutions are currently approved only for oral or intrathecal administration. Therefore, in preferred embodiments, the present invention provides high concentration baclofen solutions suitable for oral or intrathecal administration. Forms of neuraxial administration other than intrathecal administration are also preferred, such as epidural administration. In alternative embodiments, baclofen solutions of the present invention can be used for any other clinically suitable type of administration including, but not limited to, intravenous, intramuscular or subcutaneous injection.

As discussed above, current commercial preparations of baclofen consist of baclofen, sodium chloride and water. The solutions do not require any special preservation components such as antioxidants or buffers due to baclofen's high degree of chemical stability. It has been calculated that in aqueous solution at room temperature and neutral pH (pH 6 to 7) it will take 10 years before there is 10% decomposition of the dissolved baclofen. (Ahuja, 1985.) Antimicrobial preservatives are undesirable for intrathecal and epidural injections. Thus, preservatives are unnecessary.

Instead, it is the physical stability of baclofen that produces the most difficulties in a therapeutic context. Baclofen dissolves poorly in water. Once dissolved, at higher concentrations baclofen tends to precipitate out of solution after a relatively short period of time, lowering the concentration of baclofen in solution and producing undesirable particulate matter. For therapeutic reasons, any solution of baclofen intended for pharmaceutical use should meet the particulate matter requirements of the USP, 2004. Thus solutions that are likely to produce particulates during normal storage are not pharmaceutically acceptable.

Generally, baclofen solutions are obtained for pharmaceutical use either by a drug-supplier which prepares and ships the solutions to the end user or their medical care provider or pharmacist, or the solutions are prepared shortly prior to use by a medical care provider or pharmacist. Solutions that are to be used for intrathecal injection by an implanted pump must generally be stable at body temperature (37° C.) for at least about 30 days. Otherwise the baclofen solution may form unacceptable precipitates or microparticulates while in the patient's implanted pump. Therefore, the long-term stability of the baclofen solution is critical when the solution is used in these applications (e.g. stability at 37° C. of at least 30 days for solutions prepared immediately prior to injection is usually required).

Stability for longer time periods is also an issue where the drug is provided by a drug supplier that mixes the drug and ships it to the end user or their medical care provider or pharmacist. In such cases the drug may be stored, usually at room temperature or under refrigeration, for several weeks, months, or even years prior to administration. Again, it is highly desirable that the drug not form pharmaceutically-unacceptable precipitates or microparticulates either during storage prior to administration or while residing in the implanted pump prior to injection into the intrathecal space.

The inventors attempted to prepare aqueous baclofen solutions at concentrations of 3 mg/mL, 4 mg/mL, and 5 mg/mL by direct dissolution in 0.9% sodium chloride injection, USP (normal saline). The normal saline was commercially procured by the inventors and was at ambient room temperature (about 23° C.) for use in the testing. Appropriate amounts of authentic baclofen powder were weighed and added to the normal saline and shaken to aid in dissolution. Even vigorous shaking for 60 minutes did not result in complete dissolution or a clear solution at the 4-mg/mL and 5-mg/mL concentrations. Both the 4-mg/mL and especially the 5-mg/mL concentration retained large amounts of undissolved powder. The solutions were further subjected to automated shaking for one week at room temperature which still failed to result in complete dissolution. The solutions were visibly unacceptable for use as an injection. HPLC analysis of the solutions after filtration through a 0.22-micron filter to remove the undissolved powder found that the amount of baclofen actually dissolved in the normal saline in both the putative 4 mg/mL and 5 mg/mL samples was about 3.3 to 3.5 mg/mL. The inventors believe that this the concentration represents the "practical solubility" of baclofen. In practice, it is common to find that a drug's "practical solubility" is somewhat below the maximum solubility that is reported, therefore this result is unsurprising.

As used herein, the "practical solubility" is the concentration of baclofen that can be dissolved using simple practical dissolution steps such as adding the powder to an aqueous solvent and then shaking or stirring the solvent by hand or with a mechanical device. When attempting to prepare solutions having concentrations higher than the practical solubility concentration, it is common to observe residual undissolved matter, precipitation of microparticulates, or both.

Baclofen's low degree of practical solubility is likely to be the main reason that stable solutions of Baclofen are only available commercially at a concentration of 2 mg/mL. As used herein a "stable solution" means a solution containing dissolved baclofen, wherein no pharmaceutically-unacceptable quantity of undissolved baclofen is present in contact with the solution and wherein the dissolved baclofen does not precipitate out of solution to a pharmaceutically unacceptable degree for a period of at least 1 week when the solution is stored at room temperature. Typically, solutions that are stable under normal storage conditions for periods of many months or more preferably for periods of one or more years are most suitable for use as pre-prepared solutions that can be commercially supplied to end users, medical care providers or pharmacists. However, even though a solution may not be suitable for long-term storage or commercial distribution as pre-prepared solutions, solutions that are stable under normal usage conditions (i.e. for periods of at least many days or weeks, and preferably for periods of at least 30 days) can be used in applications where the solution is prepared a suitable period of time prior to administration.

Stable aqueous solutions with concentrations of baclofen higher than about 3.5 mg/mL appear not to be readily achievable by direct dissolution, as observed above. Stable aqueous solutions with concentrations of baclofen higher than about 4.3 mg/mL appeared to be impossible based upon previous observations of the upper limit of baclofen's aqueous solubility at room temperature.

As used herein "aqueous solution" means a solution that is at least 80% water by weight, preferably at least 90% water by weight, more preferably at least 95% water by weight and most preferably at least 98% water by weight. In certain embodiments, aqueous solutions of the present invention include solutions containing appropriate buffering agents, salts, preservatives, other pharmaceutically acceptable additives or any combination thereof. Alternately, aqueous solutions of the present invention can contain no such additives and can consist solely of baclofen and water. In preferred embodiments the aqueous solution of the present invention is a normal saline solution of baclofen without any further additives.

Generally, the present invention provides stable aqueous baclofen solutions at concentrations higher than the 2.0 mg/mL concentration that is currently commercially available, and methods of preparing such solutions. In particular, the present invention provides stable aqueous baclofen solutions having concentrations greater than about 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9 and 6.0 mg/mL. The present invention provides stable aqueous baclofen solutions having concentrations less than about 4.0, 4.5, 5.0, 5.5, 6.0, 6.5, 7.0, 7.5, 8.0, 8.5, 9.0, 9.5, 10.0, 10.5, 11.0, 11.5 or 12.0 mg/mL.

Any appropriate form of baclofen can be used to prepare the solutions of the present invention. In preferred embodiments, appropriate forms of baclofen include baclofen solids such as powdered, lyophilized or microfluidized baclofen. In other embodiments, the baclofen can be provided as an aqueous or non-aqueous solutions of baclofen, including buffered solutions, wherein any pharmaceutically undesirable component of said solution is either diluted to pharmaceutically-acceptable levels or removed from the final baclofen solution prior to pharmaceutical administration.

Because baclofen is stable when heated and is not subject to rapid hydrolysis, the present inventors first used a combination of heat and intense agitation to see if the solubility of baclofen at its normal neutral pH could be increased. Although it seemed counter-intuitive based on the published reports of baclofen aqueous solubility at 4.3 mg/mL in an authoritative source (Ahuja, 1985), the inventors attempted to use heat and intense agitation to achieve baclofen concentrations in normal saline of 4, 5, 6, 8, and 10 mg/mL.

The inventors observed that baclofen solutions having concentrations in the range of about 3 to about 8 mg/mL can be obtained by mixing the appropriate quantity of baclofen with an aqueous diluent and heating the solution to a temperature of at least about 30° C., at least about 40° C., at least about 50° C., preferably at least about 60° C., and most preferably at least about 70° C. and a temperature of less than about 90° C., less than about 95° C., less than about 100° C., less than about 121° C., or most preferably less than the temperature at which baclofen thermal degrades to a significant degree. The heat is applied while simultaneously subjecting the solution to intense agitation, e.g. sonication, high-speed stirring, etc. The temperature range of at least about 60° C. to at less than about 100° C. is most preferred. Further, it is generally preferable, although not required, that the aqueous solution be heated to a temperature lower than it's boiling point to prevent significant evaporation of the aqueous solvent during dissolution. Dissolution temperatures of 100° C. or higher that do not boil off the aqueous solvent can be obtained by means known to those of skill in the art, such as by increasing the atmospheric pressure that the solution is subjected to during heating. One common means of achieving this result is by autoclaving the solution.

Surprisingly, the solutions obtained through the use of heat and intensely agitation described above have enhanced physical and chemical stability characteristics. The solutions are stable for periods of at least 1, 2, 3, 4, 5, 6, 7, 8, 9, 10, 11, 12, 13, 14, 15, 16, 17, 18, 19, 20, 21, 22, 23, 24, 25 or 26 weeks, for periods of at least 7, 8, 9, 10 or 11 months, or for periods of at least 1, 1½, 2, 2½ or 3 years, depending on the concentration of baclofen in solution and the storage conditions used.

In another embodiment of the invention, stable baclofen solutions can be produced by acidification and back titration. Baclofen solutions having concentrations up to about 10.0 mg/mL can be prepared by dissolving baclofen in an acidic solution, preferably one having a pH lower than the $pKa_1$ of baclofen. For example, pH values lower than about 3.87, lower than about 3.0, lower than about 2.0, lower than about 1.5, or even lower than a pH of about 1.0 can be used advantageously. Surprisingly, once the baclofen has been dissolved in the acidic solution, and prior to pharmaceutical administration, the baclofen solution can be back titrated to a pH of 4.0 to 8.5 without precipitation of baclofen particulates. The titration is carried out by adding a base to the acidic solution until the pH is adjusted to a pH in the desired range. A final pH of 5.0 to 7.0 is currently preferred for baclofen solutions intended for pharmaceutical uses such as intrathecal injection, but pH ranges of 4.5 to 8.0 and of 4.0 to 8.5 can also be suitable for such uses. These pH ranges are intended to be illustrative of appropriate values for uses such as intrathecal injection. The appropriate pH ranges for any particular pharmaceutical application will be readily apparent to those skilled in the art, and the final pH of the baclofen solution can be any pharmaceutically acceptable pH appropriate for a given use. In addition, baclofen solutions prepared by this method can be stored at a pH that is not appropriate for a given pharmaceutical use so long as the solution is titrated to a pharmaceutically acceptable pH prior to administration.

In preferred embodiments, the acid or acids used to produce the acidic solution are pharmaceutically acceptable acids such as hydrochloric acid, sulfuric, phosphoric, acetic, tartaric, fumaric acid and the like.

In other embodiments, the acidic solution is further subjected to heat (as described above) intense agitation (as described above) or both to speed or enhance the dissolution of the baclofen or to improve the stability of the aqueous baclofen solution being prepared.

Alternately, stable baclofen solutions can be produced by alkalinization and back titration. That is, solutions having concentrations of baclofen of about 10.0 mg/mL or lower can be prepared by dissolving baclofen in a basic solution, preferably one having a pH higher than the $pKa_2$ of baclofen. For example, solutions of pH higher than about 9.62, higher than about 10.0, higher than about 11.0, higher than about 12.0, and even higher than the pH of about 13.0 can be used advantageously. Once the baclofen is dissolved in the basic solution the pH can be back titrated to a pH of about 4.0 to 8.5, or preferably can be titrated to a pH of 5.0 to 7.0, or to other pH values appropriate for pharmaceutical uses such as intrathecal injection, as discussed above. For use in other applications, pharmaceutical or otherwise, or during storage prior to use the baclofen solution can be titrated to a lower pH or can be maintained for some period of time at the original basic pH.

In preferred embodiments, the base or bases used to produce the basic solution are pharmaceutically acceptable bases such as sodium hydroxide, potassium hydroxide and the like.

In other embodiments, the basic solution is further subjected to heat (as described above) intense agitation (as described above) or both to speed or enhance the dissolution of the baclofen or to improve the stability of the aqueous baclofen solution being prepared.

Surprisingly, the solutions obtained by dissolution of baclofen in acidic or basic solutions also have enhanced physical and chemical stability characteristics both before and after back titration to a more neutral pH. The solutions are stable for periods of at least 1, 2, 3, 4, 5, 6, 7, 8, 9, 10, 11, 12, 13, 14, 15, 16, 17, 18, 19, 20, 21, 22, 23, 24, 25 or 26 weeks, for periods of at least 7, 8, 9, 10 or 11 months, or for periods of at least 1, 1 ½, 2, 2 ½ or 3 years, depending on the concentration of baclofen in solution and the storage conditions used.

It alternate embodiments, the acidic or basic solution of baclofen can be lyophilized to form a powder that is reconstituted and back titrated prior to use. Such embodiments would be especially useful for preparing solutions having very high concentrations of baclofen, e.g. 6.0 mg/mL or higher, that are stable for a period of time that is pharmaceutically acceptable for a given use, but that is not acceptable for a solution that is commercially distributed as a pre-prepared solution. For example, solutions of baclofen of about 8.0, of about 10.0, or higher than about 10.0 mg/mL can be readily prepared for immediate use in instances where the solution is not required to be stable for a period of more than a few days or weeks.

In further embodiments, stable baclofen solutions of the present invention can be provided in a medical package of baclofen solution suitable for injection or oral administration. In preferred embodiments, the medical package contains a solution that is compatible with cerebrospinal fluid and therefore suitable for intrathecal administration. Typically, medical packages suitable for intrathecal administration will include a sterile, isotonic solution of baclofen free of pyrogens, antioxidants, preservatives or other potentially neurotoxic additives. In related embodiments the medical package will comprise one or more single dose containers (e.g. ampules) of a sterile baclofen solution that is suitable for oral or parenteral administration with or without dilution prior to administration.

In general, baclofen is introduced to the cerebrospinal fluid by means of administration by direct injection, administration via an external intrathecal pump or administration via an internal intrathecal pump, wherein the pump itself is implanted into the abdomen of the patient. The internal pumps are often refilled by means of an injection through the skin of the patient into a reservoir in the pump designed to receive the solution to be administered. The present invention provides medical packages suitable for use with any of these routes of administration, including single use or multi-use medical packages for use in direct injection or in the filling or refilling of external or internal intrathecal pumps.

Furthermore, the embodiments of the present invention can be combined to enhance the effectiveness of the methods described above. For example, baclofen solutions can be dissolved in an acidic solution that is heated or subjected to intense agitation or both, or baclofen solutions can be dissolved in a basic solution that is heated or subjected to intense agitation or both.

. . .

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Materials. Baclofen, U.S.P., powder and drug reference standard and 0.9% sodium chloride injection, U.S.P. is obtained from commercial sources. Analytical mobile phase components are HPLC grade and purchased commercially. For packaging of the various solutions in syringes, 30-mL Becton-Dickinson syringes are used, fitted with Braun Luer lock "Red Cap" syringe tip seals. Becton-Dickinson needles are used to effect the drug transfers. The syringes, needles, and seals are purchased through commercial sources. Similarly, empty sterile 30-mL glass vials are purchased from a commercial source.

Methods of Sample Preparation. All manipulations are conducted in a Class 100 environment in a biological, safety cabinet. Each test solution is prepared as a pooled sample and then subdivided by (1) drawing 20 mL of the solution into 30-mL Becton-Dickinson syringes having Braun Luer lock "Red Cap" syringe tip seals and (2) sealing the Luer tip with a Red Cap Luer tip seal and (3) filling 20 mL of the test solution into 30-mL sterile empty glass vials. Separate sample syringes and sample vials are prepared for each drug concentration at each storage temperature. Separate syringes and vials are prepared for analysis of the drug content. Further syringes and vials are used to evaluate the physical stability of the solutions.

Methods of Sampling and Analysis. Each pooled solution is analyzed and evaluated immediately after preparation. This serves as the initial time point evaluation for the test solution. The solution is then packaged into the syringes and vials as noted under Sample Preparation.

The test solutions in vials and syringes are thoroughly mixed prior to sampling. A 1-mL sample of each test solution from three test syringes and three test vials is collected and chemically analyzed. The sample aliquots are removed from each container after 1, 3, 7, 14, 21, 30 and 60 days of storage at 4° C., 23° C., and 37° C. Triplicate HPLC determinations are performed at each time point if needed to determine the maximum stability of baclofen. The contents of the remaining containers are visually inspected at each assay time point and 6-mL samples are collected and fully evaluated for physical stability as indicated under Physical Stability Evaluation above after 1, 3, 7, 14, 21, 30 and 60 days.

EXAMPLE 1

Solubilization of Baclofen by Heat and Sonication. Appropriate amounts of baclofen were weighed and added to appropriate volumes of normal saline in order to produce mixtures containing 4, 5, 6, 8 or 10 mg/mL baclofen. All samples had undissolved baclofen powder present immediately after mixing. Samples having concentrations of 4, 5 or 6 mg/mL of baclofen were heated to 70° C. Samples having concentrations of 8 and 10 mg/mL of baclofen were heated to 95° C. Intense agitation was applied to all of the samples by sonicating the samples during the heating step. Heating and sonication were continued until all of the powder dissolved, and a clear solution with no residual particulate matter resulted. For the 4, 5, and 6 mg/mL samples, this occurred in about 20 to 30 minutes. The increased heating and sonication for higher concentrations resulted in dissolution in about 20 minutes for the 8 and 10 mg/mL samples. Again, the solutions were clear with no residual particulate matter.

After complete dissolution of the samples had occurred, the solutions were allowed to cool to room temperature and several separate aliquots of each sample were filtered through 0.22-micron sterilizing filters into sterile empty vials. Vials containing samples of each solution were stored under one of three test conditions: vials were stored at room temperature or under refrigeration (to simulate normal storage conditions), or at 37° C. (to simulate "in use" conditions in an implanted pump).

EXAMPLE 2

Solubilization of Baclofen by Heat and High-Speed Stirring. Appropriate amounts of baclofen were weighed and added to appropriate volumes of normal saline in order to produce mixtures containing 4, 5, 6, 8 or 10 mg/mL baclofen. All samples had undissolved baclofen powder present immediately after mixing. Samples having concentrations of 4, 5 or 6 mg/mL of baclofen were heated to 70° C. Samples having concentrations of 8 and 10 mg/mL of baclofen were heated to 95° C. Intense agitation was applied to all of the samples by high-speed stirring. A high-speed stir bar was placed in each of the containers for each of the baclofen concentrations was stirred using a Thermolyne stirrer at a speed of about 600 rpm while the solutions were heated. This was designed to simulate the use of a high-speed high shear mixer in a larger industrial setting. Again the heating at 70° C. for the 4, 5, and 6 mg/mL concentrations and to 95° C. for the 8 and 10 mg/mL concentrations and high-speed stirring were continued until all of the powder had dissolved and a clear solution with no residual particulate matter resulted. This occurred within about 20 minutes with all samples.

After complete dissolution of the samples had occurred, the solutions were allowed to cool to room temperature and several separate aliquots of each sample were filtered through 0.22-micron sterilizing filters into sterile empty vials. Vials containing samples of each solution were stored under one of three test conditions: vials were stored at room temperature or under refrigeration (to simulate normal storage conditions), or at 37° C. (to simulate "in use" conditions in an implanted pump).

EXAMPLE 3

Acidification with Back Titration. Baclofen concentrations of 4, 5, 6, 8, and 10 mg/mL were prepared by dissolving appropriate amounts of baclofen powder in 0.1 N hydrochloric acid. The baclofen powder readily dissolved within a few minutes and a clear solution with no residual particulate matter resulted. The solutions were then back titrated with 0.1 N sodium hydroxide to reach a pH about 5.0 to 5.1, which is within the current product pH range for commercial baclofen solutions, and brought to volume with 0.9% sodium chloride. After complete dissolution had occurred, the solutions were filtered through 0.22-micron sterilizing filters into sterile empty vials. The vials were stored at room temperature, under refrigeration, and at 37° C. to simulate "in use" conditions in an implanted pump.

EXAMPLE 4

Alkalinization with Back Titration. Baclofen concentrations of 4, 5, 6, 8, and 10 mg/mL were prepared by dissolving appropriate amounts of baclofen powder in 0.1 N sodium hydroxide. The baclofen powder readily dissolved within a few minutes and a clear solution with no residual particulate matter resulted. The solutions were then back titrated with 0.1 N hydrochloric acid to reach a pH about 6.9 to 7.0, which is within the current product range, and brought to volume with 0.9% sodium chloride. After complete dissolution had occurred, the solutions were filtered through 0.22-micron sterilizing filters into sterile empty vials. The vials were stored at room temperature, under refrigeration, and at 37° C. to simulate "in use" conditions in an implanted pump.

EXAMPLE 5

Testing of Solubility Under Various Storage Conditions. Baclofen 4 mg/mL solutions prepared with heat and sonication (Example 1) as well as the 4 mg/mL solutions prepared with heat and high speed stirring (Example 2) have stayed in solution, remaining clear and free of visible particulates and unacceptable microparticulates, for over 12 months at room temperature and for at least one month at 37° C. (the maximum duration tested). Particularly notable is the observation that the solutions even remained in solution when refrigerated at 4° C. for at least 60 days (the maximum duration tested).

Baclofen 4 mg/mL solutions prepared by pH adjustment (Examples 3 and 4) and baclofen 5 and 6 mg/mL solutions prepared by all four methods (Examples 1-4) have also remained clear and free of unacceptable microparticulates when stored either at room temperature or at 37° C. for at least 60 days. However, when subjected to refrigeration, the 5 and 6-mg/mL concentrations developed a precipitate after 14 days and 7 days, respectively.

EXAMPLE 6

Physical stability of 8.0 mg/mL baclofen solutions. Most surprising because of the high concentration, the baclofen 8-mg/mL solution prepared by acidification and back titration to pH 5 (Example 3) remained in solution clear and free of unacceptable microparticulates for at least 30 days at room temperature.

EXAMPLE 7

Physical stability of 8.0 mg/mL baclofen solutions. The 8-mg/mL solution prepared by alkalinization and back titration (Example 4) remains in solution clear and free of unacceptable microparticulates for at least 30 days at room temperature.

EXAMPLE 8

Physical stability of 8.0 mg/mL baclofen solutions. The 8-mg/mL solution prepared by heating and agitation (Examples 1 and 2) remained clear and free of unacceptable microparticulates for only 14 days at room temperature or at 37° C. before developing some trace particulate precipitation.

EXAMPLE 9

Physical stability of 10.0 mg/mL baclofen solutions. Initially a clear and particle-free baclofen 10-mg/mL solution was prepared using each of the methods disclosed in Examples 1 through 4. However, upon standing at room temperature, crystalline precipitation developed within 1 or 2 days in all of the 10 mg/mL samples.

EXAMPLE 10

HPLC Analysis to Confirm Baclofen Concentration. A stability-indicating HPLC analytical method adapted from published methods was used to determine the concentration of the baclofen samples evaluated in this testing (Sitaram et al., 1997; Gupta et al., 1998; Johnson CE, et al., 1993; Allen LV, et al., 1996. This method was used to document that at the higher concentrations the entire amount of baclofen had dissolved, and the solutions were near the target concentrations. All tested sample solutions were filtered through 0.22-micron filters to remove remaining undissolved drug, if any, prior to analysis. The HPLC analytical method used is cited in Tables 1 and 2. Analysis of the finished solution demonstrated that all of the baclofen had indeed dissolved. Initial baclofen concentrations for the nominally 4, 5, 6, and 8 mg/mL test solutions were within 93 to 104% of the target concentrations.

TABLE 1

HPLC Analytical Method Used

Baclofen[a]

| | |
|---|---|
| Column: | Symmetry $C_{18}$, 5 μm, 250 × 4.6 mm i.d. |
| Mobile Phase: | A. 0.085 M ammonium phosphate 78.5% and acetonitrile 21.5% |
| | B. Acetonitrile 100% |
| Flow Rate: | Gradient. See Table 2. |
| Detection: | UV 220 nm, 1.0 AUFS |
| Retention Times: | |
| Baclofen | 4.7 min |
| Decomposition products | 3.3, 6.4, 17 min |

[a]Precision: Mean ± S.D. (n = 10) 99.8 ± 1.0 μg/mL; percent relative standard deviation was 1.0%. Standard curves range was baclofen 50 to 150 μg/mL. Correlation coefficients were >0.9999.

TABLE 2

HPLC Mobile Phase Gradient Table

| Time (min) | Flow (mL/min) | A (%) | B (%) |
|---|---|---|---|
| 0 | 0.8 | 100 | 0 |
| 5 | 0.8 | 100 | 0 |
| 6 | 1.0 | 77 | 23 |
| 13 | 1.0 | 77 | 23 |
| 15 | 1.0 | 100 | 0 |
| 23 | 1.0 | 100 | 0 |
| 25 | 0.8 | 100 | 0 |

The liquid chromatograph is a Waters LC Module-1 Plus having a multisolvent pump, variable wavelength UV detector, and autosampler in one unit. The system is also controlled and integrated by a personal computer running chromatography management software.

EXAMPLE 11

Physical Stability Evaluation. The samples are also evaluated for changes in turbidity and particulate formation. In addition to visual inspection in normal diffuse fluorescent room light and using a high-intensity monodirectional light source (Tyndall beam) against a dark background, turbidity is measured using a Hach Company model 2100AN color-correcting turbidimeter, and particle sizing/counting is performed using a light-obscuration particle sizer and counter (HIAC-Royco Model 9703 particle sizer/counter).

EXAMPLE 12

Shelf-Life Evaluation. The 4-mg/mL samples prepared with heat and sonication (Example 1) and with heat and high-speed stirring (Example 2) remained in solution for at least one year with no loss of drug at room temperature of 23° C. Furthermore, the samples have remained clear and free of visible particulates and microparticulate precipitation during that time period.

EXAMPLE 13

Shelf-Life Evaluation. Baclofen solution at concentrations of 3.0 mg/mL, 3.5 mg/mL and 4.0 mg/mL were prepared by heat and sonication as in Example 1 and were stored at room temperature for a period of 24 months. At 24 months, the physical stability of the samples was assessed as in Example 11 and were found to be physically stable by all four methods, that is, all the tested samples were clear and showed an absence of particulates. The results of the chemical stability studies are also given in Table 3. The chemical stability of the samples was assessed by HPLC as in Example 10. The percentage of sample remaining in solution for each sample is given in Table 3.

Additional baclofen solutions at concentrations of 4.0 mg/mL, 5.0 mg/mL, 6.0 mg/mL and 8.0 mg/mL were prepared by heat and sonication as in Example 1 and were stored at room temperature for a period of over 16 months. The physical and chemical stability of the samples was assessed at 12 months. As shown in Table 3, at twelve months the 4.0 and 5.0 mg/mL solutions remained clear and no particulates were detected by the methods described in Example 11. Visual inspection of the samples at approximately 16 months showed no change in the solutions. Also as shown in Table 3, at twelve months the 6.0 mg/mL solution was shown to have no visible particulates to the unaided eye, but did contain trace amounts of solid material. These solutions containing trace amounts of particulates would generally still be considered pharmaceutically acceptable. Visual inspection of this sample at approximately 16 months showed no change in its condition. The 8.0 mg/mL solution remained in solution for at least 30 days, but between day 30 and 60 the baclofen fell out of solution and the sample was not evaluated further.

TABLE 3

Shelf-life Stability of High Concentration Baclofen Injection Stored at Room Temperature

| Baclofen Concentration (mg/mL) | Test Period (months) | Physical Stability (yes/no) | Chemical Stability (% Remaining) |
|---|---|---|---|
| 3 mg/ml | 24 | yes | 101.7 ± 1.0[a] |
| 3.5 mg/ml | 24 | yes | 100.0 ± 0.4[a] |
| 4 mg/ml | 24 | yes | 99.5 ± 1.2[a] |
| 4 mg/ml | 12 | yes | 99.9 ± 0.5 |
| 5 mg/ml | 12 | yes | 100.6 ± 0.5 |
| 6 mg/ml | 12 | yes[b] | 102.9 ± 1.0 |

[a]Chemical stability testing did not start until six months after preparation. The 24-month concentrations were calculated based on the concentrations measured at six months. the physical stability was evaluated from study start date.
[b]No visible particulates to the unaided eye. However, a few vials developed a small amount of trace microparticulates, mostly one or two microns in size, after 4 months of storage.

All of the compositions and methods disclosed and claimed herein can be made and executed without undue experimentation in light of the present disclosure. While the compositions and methods of this invention have been described in terms of preferred embodiments, it will be apparent to those of skill in the art that variations can be applied to the compositions and/or methods and in the steps or in the sequence of steps of the methods described herein without departing from the concept, spirit and scope of the invention. More specifically, it will be apparent that certain agents that are chemically or physiologically related can be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

1. Sitaram B. R., Tsui M., Rawicki H. B., et al., "Stability and compatibility of intrathecal admixtures containing baclofen and high concentrations of morphine", *Int. J. Pharm.*, 1997, 153: 13-24;
2. Gupta V D, Parasrampuria J., "Quantitation of 4-(4-chlorophenyl)-2-pyrrolidine in baclofen powder and tablets," *Drug Develop. Indust. Pharm.*, 1998, 14: 1623-1628.
3. McEvoy G., *AHFS Drug Information* 2003, Bethesda, Md.: American Society of Health-System Pharmacists, 2003.
4. Ahuja S., "Baclofen," *Analytical Profiles of Drug Substances*, Vol. 14, New York: Academic Press, 1985, pp. 527-548.
5. Lioresal Intrathecal package insert, Medtronic Neurological, Minneapolis, Minn., April, 1997.
6. USP Dictionary of USAN and International Drug Names 2003, Rockville, Md.: United States Pharmacopeial Convention, 2003.
7. United States Pharmacopeia $27^{th}$ ed., Rockville, Md.: United States Pharmacopeial Convention, 2004.
8. Johnson C. E., et al., "Stability of an extemporaneously compounded baclofen oral liquid", *Am. J. Hosp. Pharm.*, 1993, 50:2353-55.
9. Allen L. V., et al., "Stability of Baclofen, Captopril, Diltiazem Hydrochloride, Dipyridamole, and Flecainide Acetate is Extemporaneously Compounded Oral Liquids", *Am J Health-Syst. Pharm.*, 1996, 53:2179-2184.
10. Cruaud et al., "The Characterization and Release Kinetics Evaluation of Baclofen Microspheres Designed for Intrathecal Injection", *Int. J. Pharmacuetics*, 177, 1999, 247-257).

What is claimed is:

1. A solution consisting of baclofen at a concentration of 4.0 mg/mL in normal saline, wherein the solution is stable for at least 30 days at room temperature.
2. The solution of claim 1, wherein the solution is stable for at least 12 months at room temperature.
3. The solution of claim 1, wherein the solution is stable for at least 60 days at 37° C.
4. The solution of claim 1, wherein the solution is stable for at least 24 months at room temperature.

* * * * *